United States Patent [19]

Pawliszyn

[11] Patent Number: 5,691,206

[45] Date of Patent: Nov. 25, 1997

[54] METHOD AND DEVICE FOR SOLID PHASE MICROEXTRACTION AND DESORPTION

[76] Inventor: Janusz B. Pawliszyn, 383 Dunvegan Drive, Waterloo, Ontario, Canada, N2K 1W7

[21] Appl. No.: 306,435

[22] Filed: Sep. 19, 1994

Related U.S. Application Data

[63] Continuation-in-part of Ser. No. 934,736, filed as PCT/CA91/00108, Apr. 2, 1991, abandoned.

[30] Foreign Application Priority Data

Apr. 2, 1990 [GB] United Kingdom .................... 9007356

[51] Int. Cl.$^6$ ........................................... G01N 1/18
[52] U.S. Cl. .................... 436/178; 422/58; 73/863.21; 73/54.42; 73/61.43; 73/61.59; 73/61.76; 73/64.56
[58] Field of Search ........................ 436/178, 177; 422/58, 69; 73/863.21, 335.11, 335.13, 54.42, 61.43, 61.59, 61.76, 64.56; 604/164, 11–15; 356/417; 385/12

[56] References Cited

U.S. PATENT DOCUMENTS

| | | | |
|---|---|---|---|
| 4,488,814 | 12/1984 | Johnson | 356/417 |
| 4,949,038 | 8/1990 | Birch et al. | 385/12 |
| 4,974,927 | 12/1990 | Curry | 385/12 |

OTHER PUBLICATIONS

Pawliszyn et al. Anal. Chem. 1987, 59, 1475–1478, "Sample Introduction for Capillary . . . ".

*Primary Examiner*—James C. Housel
*Assistant Examiner*—Rachel Heather Freed
*Attorney, Agent, or Firm*—Daryl W. Schnurr

[57] ABSTRACT

A device for carrying out solid phase microextraction is a fiber contained in a syringe. The fiber can be solid or hollow. The syringe has a barrel and a plunger slidable within the barrel, the plunger having a handle extending from one end of the barrel. A hollow needle extends from an end of the barrel opposite to the plunger. The fiber is contained in the needle. When the plunger is depressed, the fiber extends beyond a free end of the needle and when the plunger is in a withdrawn position, the fiber is located within the needle. The syringe protects the fiber from damage. When it is desired to analyze a sample in a bottle having a septum, the needle is inserted through the septum and the plunger is depressed so that the fiber will extend into the sample. After one or two minutes, the plunger is moved to the withdrawn position so that the fiber will return to the needle and the syringe is withdrawn from the sample bottle. The syringe is then inserted through a septum in a gas injection port of a gas chromatograph. The plunger is again depressed so that the fiber will extend into the gas chromatograph and an analysis of the components on the fiber is carried out. Then, the plunger is moved to the withdrawn and the syringe is withdrawn from the injection port. Previously, samples were analyzed using liquid-liquid extraction or using cartridges. Both of these methods are relatively expensive and time consuming. Both of these methods also require the use of solvents which can be difficult and expensive to dispose of.

32 Claims, 9 Drawing Sheets

METHOD AND DEVICE FOR SOLID PHASE MICROEXTRACTION AND DESORPTION

This is a continuation-in-part application of application Ser. No 07/934,736, filed as PCT/CA91/00108 Apr. 2, 1991, now abandoned.

BACKGROUND OF THE INVENTION

1. Field of the Invention

This invention relates to a method and device for solid phase microextraction and analysis and, in particular, relates to microextraction and analysis being carried out using various types of a single fiber which can be coated with various materials or uncoated.

2. Description of the Prior Art

Presently, in the organic analysis of environmental samples which involve the separation of components of interest from such matrices as soil, water, fly ash, tissue or other material, liquid extraction is tradionally used as the separation process. For example, water samples are usually extracted with organic solvent. Similarly, solid samples are leeched with an organic solvent in a SOXHLET apparatus. Methods based on solvent extraction are often time consuming, difficult to automate and are very expensive since they require high purity organic solvents and these organic solvents are expensive to dispose of. Further, the organic solids usually have high toxicity and are difficult to work with. In addition, the extraction processes can be highly non-selective. Therefore, sequential chromatographic techniques must sometimes be used to separate complex mixtures after extraction, significantly increasing the overall analysis time and the cost. EP-A1-159 230 discloses an extraction method of components in a liquid by placing packets of fibers in contact with said liquid in extracting the components.

Solid phase extraction is a known effective alternative to liquid-liquid extraction in the analysis aqueous samples. The primary advantage of solid phase extraction is the reduced consumption of high purity solvents and the resulting reduction in laboratory costs and the costs of solvent disposal. Solid phase extraction also reduces the time required to isolate the analyte of interest. However, solid phase extraction continues to use solvents and often suffer; from high blank values. Further, there is considerable variation between the products offered by different manufacturers and lot-to-lot variation can be a problem when carrying out solid phase extraction procedures. Solid phase extraction cartridges available for manufacturers are normally constructed of plastic which can adsorb the analyte and increase interferences in the analysis. The disposable plastic cartridges used in the solid phase extraction process are first activated using organic solvent. The excess organic solvent is then removed and the sample to be tested is passed through the cartridge. The organic components from the sample are adsorbed on the chemically modified silica surface of the material in the cartridge. Both molecules of interest as well as interferences are retained on the cartridge material. During desorption, a selective solvent is chosen to first remove the interferences. The analyte is then washed out of the cartridge. The analytical procedure from that point is identical to that used in liquid-liquid extraction. The analyte is first preconcentrated and the mixture is then injected into an appropriate high resolution chromatographic instrument. Steps involving the use of organic solvents are the most time consuming.

SUMMARY OF THE INVENTION

A device for carrying out solid phase microextraction of components contained in a fluid carrier is characterized by, in combination, a fiber and a housing surrounding said fiber, said fiber being mounted to a movable part in said housing so that said fiber is movable longitudinally within said housing. The movable part is movable over a sufficient distance to expose a sufficient length of fiber outside of said housing to permit microextraction to occur. The movable part is able to successively expose a length of fiber outside of said housing to said carrier and retract said fiber into said housing out of contact with said carrier.

A method of carrying out solid phase microextraction and analysis with components contained in a carrier uses a fiber. The method is characterized by the steps of choosing either the fiber or a coating for the fiber based on selectivity of the fiber or coating chosen to at least one component in said carrier, contacting said fiber with said carrier containing said components for a sufficient period of time for chemical extraction to occur with said at least one componet, subsequently removing said fiber from said carrier and placing the fiber into a suitable analytical instrument and carrying out desorption with respect to at least one component on said fiber.

A method of carrying out solid phase microextraction and analysis with components contained in a carrier uses a fiber contained in a housing. The housing has access means so that said carrier can be brought into contact with said fiber. The method is characterized by contacting said fiber with said housing for a sufficient time to allow chemical extraction to occur, ending said contact and placing said fiber in a suitable analytical instrument in such a manner that desorption occurs with respect to at least one component on said fiber.

BRIEF DESCRIPTION OF THE DRAWINGS

FIG. 7b shows a chromatogram produced when using the prior art method of liquid-liquid extraction for the same components as those of FIG. 7a;

DESCRIPTION OF A PREFERRED EMBODIMENT

Figure 1:
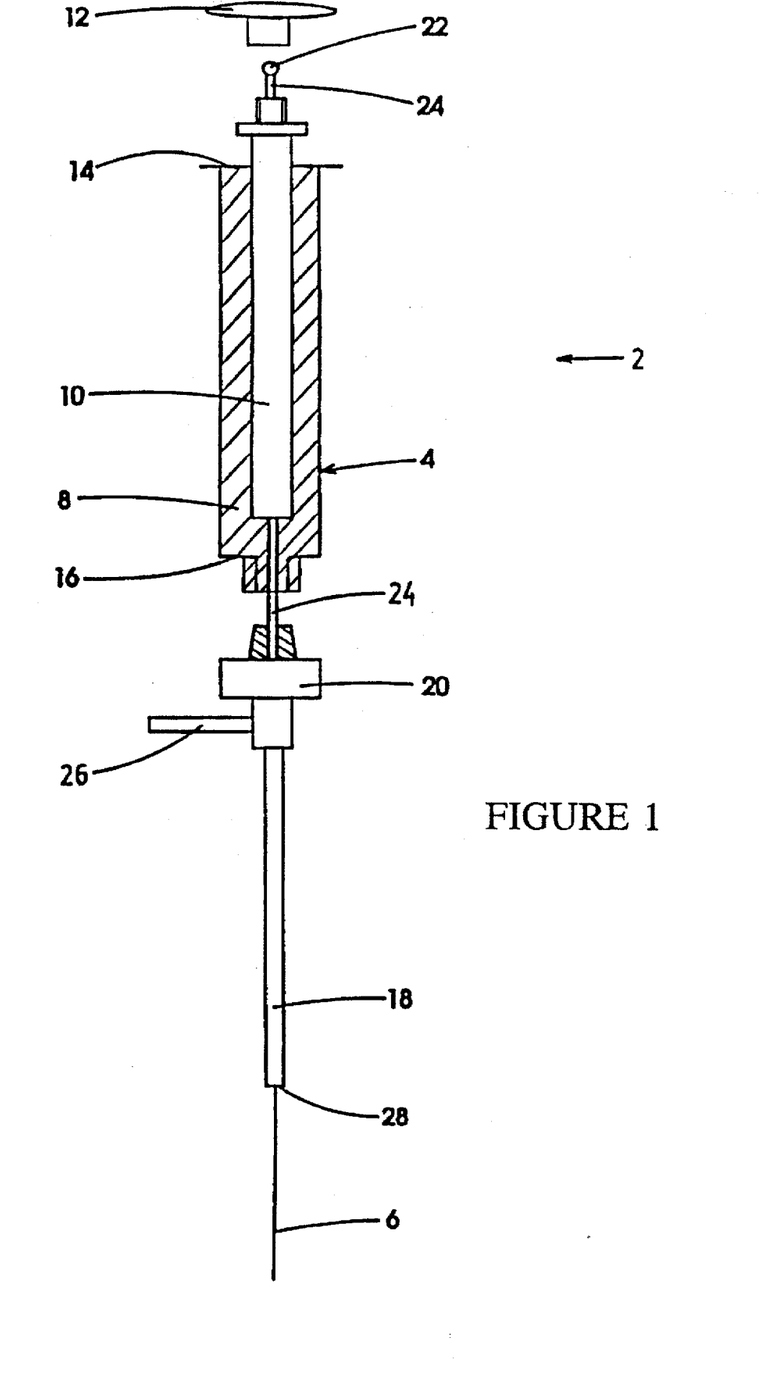
FIG. 1 is a partial sectional side view of a syringe and fiber with the plunger depressed.
Figure 2:
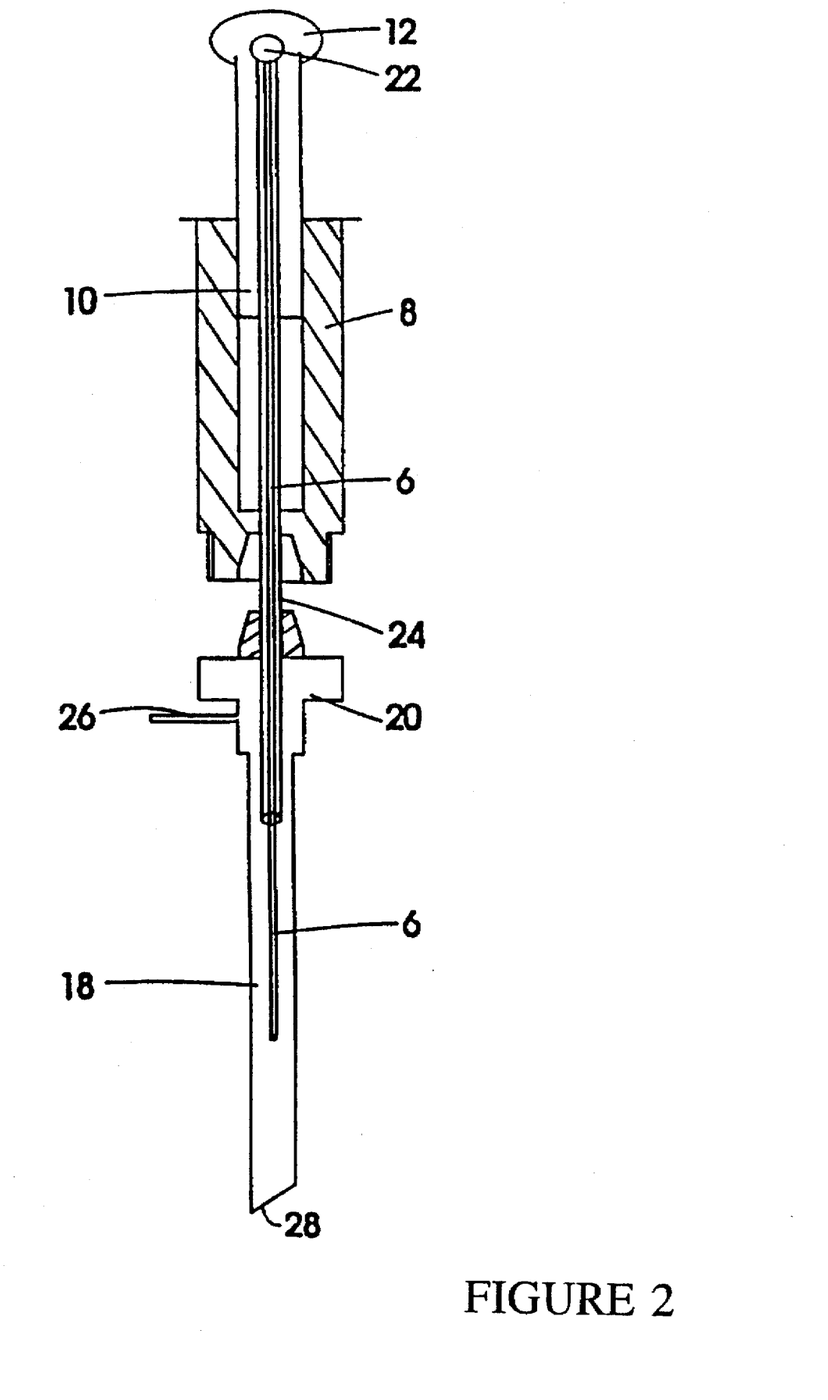
FIG. 2 is a schematic side view of a slightly different syringe and fiber with the plunger withdrawn.

Referring to FIGS. 1 and 2 in greater detail, a device 2 for carrying out solid phase microextraction has a syringe 4 containing a fiber 6. The syringe 4 is made up of a barrel 8 which contains a plunger 10 and is slidable within the barrel 8. The plunger 10 has a handle 12 extending from one end 14 of the barrel 8. At the opposite end 16 of the barrel 8, there is located a needle 18 which is connected to the end 16 by the connector 20. The handle 12 and the needle 18 and connector 20 are shown in an exploded position relative to the barrel 8 for ease of illustration.

The fiber 6 is a solid thread-like material that extends from the needle 18 through the barrel 8 and out the end 14. An end of the fiber 6 (not shown) located adjacent to the cap 12 has retention means 22 located thereon so that the fiber will move longitudinally as the plunger 10 slides within the barrel 8. The retention means can be simply a drop of epoxy which is placed on the end of the fiber 6 near the handle 8 and allowed to harden. The fiber 6 is partially enclosed in a metal sleeve 24 which surrounds that portion of the fiber 6 located within the plunger 10, the barrel 8 and part of the needle 18. The purpose of the metal sleeve 24 is to protect the fiber 6 from damage and to ensure a good seal during operation of the device. Extending from the connector 20 is an optional inlet 26. The purpose of the inlet 26 is to allow alternate access to the fiber. For example, when the fiber is contained within the needle 18, fluid could contact the fiber 6 by entering the inlet 26 and exiting from a free end 28 of the needle 18. The inlet 26 can also be used to contact the fiber with an activating solvent.

In FIG. 2, a schematic version of the device 2 is shown. The plunger is in a withdrawn position and the free end of the fiber 6 is located entirely within the needle 18. The access permitted by the inlet 26 when the fiber is in the position shown in FIG. 2 can readily be understood. Obviously, fluid contacting the fiber 6 within the needle 18 could also enter the free end 28 of the needle 18 and exit from the access 26.

Figure 3:
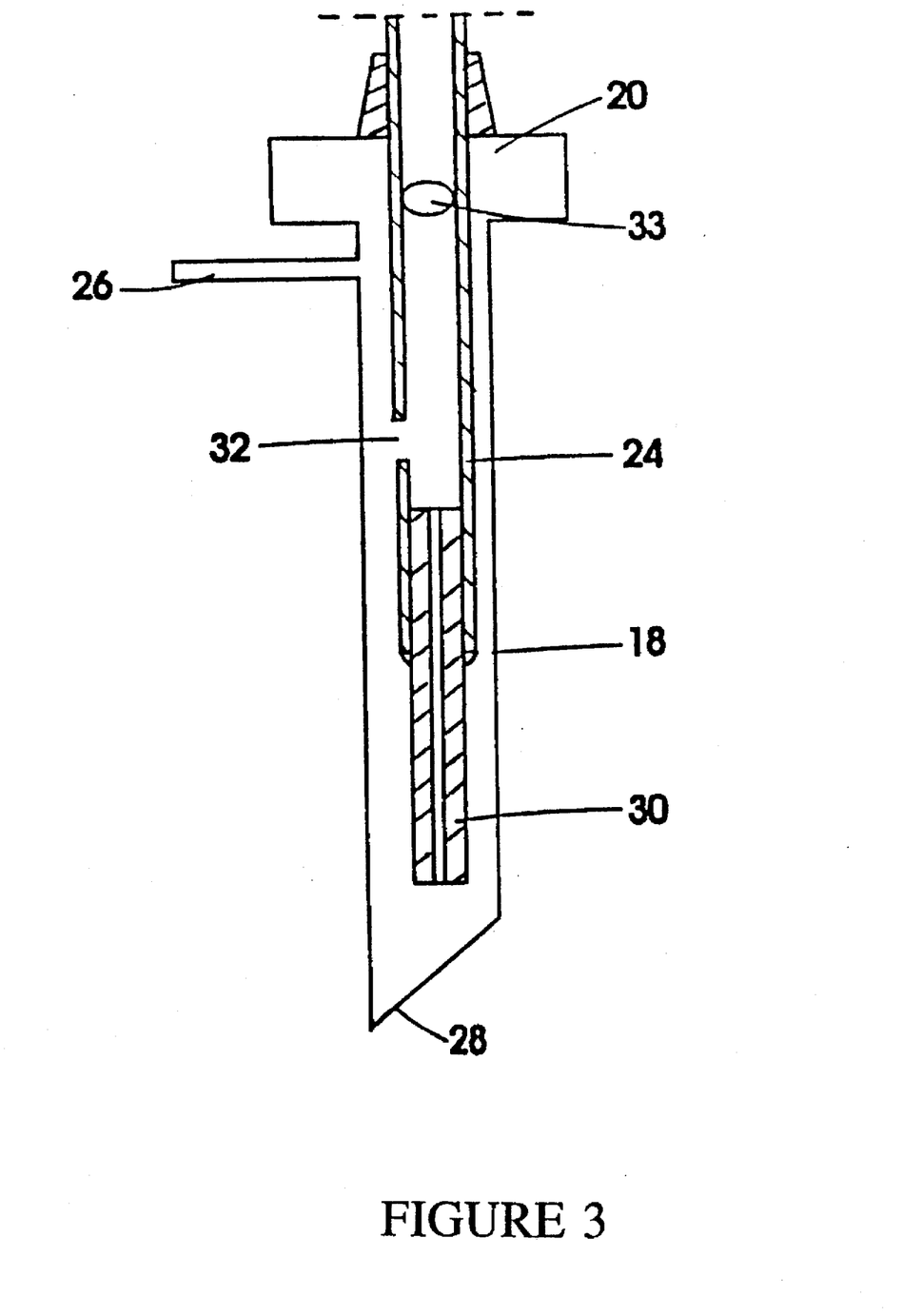
FIG. 3 is a schematic side view of a needle portion of a syringe containing a hollow fiber.

In FIG. 3, only the needle portion of the device is shown. A fiber 30 extending from the metal sleeve 24 is hollow. It can be seen that there is an opening 32 in the wall of the metal sleeve 24 to allow access to an interior of the sleeve 24 as well as an interior of the fiber 30. For example, fluid could enter the inlet 26 and an interior of the needle 18. Then, the fluid could pass through the opening 32 and through an interior of the fiber 30 and ultimately exit from the free end 28 of the needle 18. In this embodiment, the fiber does not extend to the handle 12 (not shown) but only the metal sleeve 24 extends to the handle 12. The fiber 30 can still be moved beyond the end 28 of the needle 18 by depressing the plunger and returned to the position shown in FIG. 3 by moving the plunger to the withdrawn position.

Alternatively, if it is desired to have the fiber 30 located within the needle 18 at all times, contact with the fiber 30 can be attained through the inlet 26 or the opening 32 and the free end 28. A plug 33 located within the metal sleeve 24 prevents any fluid from travelling up the sleeve to the handle. In some situations, the fluid could flow through the sleeve 24.

In general terms, the syringe could be said to be a housing for the fibers 6, 30 and the access means could be the action of the plunger 10 in moving the fiber beyond the end 28 or, alternatively, the access means could be the inlet 26.

The disadvantages and inconveniences of the previous processes for analyzing various fluids are overcome by the solid phase microextraction technique of the present invention. The diameter of the fibers will vary but will preferably be between 0.05 millimeters and 1 millimeter. Much of the experimentation on which the present invention was based, was carried out using fused silica fibers that were chemically modified. The fused silica fibers are widely used in optical communication and are often referred to as optical fibers.

Chemical modification of these fibers can be achieved by the preparation of the surface involving etching procedures to increase the surface area followed by chemical attachment of the desired coating. The stationary phases bonded to the surface of the silica fibers are similar to that used in fused silica gas chromatograph columns or high performance liquid chromatography columns.

As an example, fused silica fibers were obtained from Polymicro Technologies Inc., Phoenix, Ariz. and these fibers were coated with polyimide and had an outer diameter of approximately 171 µm. Uncoated fused silica was obtained by burning off the polyimide coating and gently scraping off the charred portion. To use the polyimide film as a stationary phase, it was first heated at 350° C. for four hours. The polyimide was then burned off and the char removed, except for a one to two millimeter portion at the end of the fiber. In all cases, the polyimide was burned off after the fiber had been inserted into the syringe and trimmed to the correct length. After burning, the fiber became fragile and had to be handled carefully. The metal casing is used to strengthen the fiber. The normal lifetime for a prepared fiber was five to six weeks with regular use.

The solid phase microextraction process does not require a sophisticated coating system to be a useful technique. Either the uncoated fiber, fused silica, silicone or the polyimide films that optical fibers are shipped with can be a suitable stationary phase.

The method of solid phase microextraction and analysis consists of a few simple steps. For example, when a water matrix sample containing components of interest is desired to be analyzed, the plunger of the syringe is depressed and the exposed fiber extending from the free end of the needle is inserted into the water matrix sample. The organic components of the water are extracted into the non-polar phase. Water is considered to be the carrier in a water matrix sample. Where the water sample is contained in a bottle containing a septum, the needle is inserted through the septum first before the plunger is depressed so that the fiber will not be damaged by the septum. When the microextraction has occurred to a sufficient degree (usually approximately two minutes), the plunger is moved to the withdrawn position causing the fiber to be drawn into the needle and the needle is removed from the sample bottle through the septum. Preferably, the sample is stirred while the fiber is inserted. The time for extraction will depend on many factors including the components being extracted as well as the thickness and type of coating, if any, on the fiber. Usually, the extraction time is approximately two minutes. The plunger is then moved to the withdrawn position to retract the fiber into the needle. The needle is then removed from the bottle and is inserted through the septum in an injection port of a conventional gas chromatograph or other suitable analytical instrument. The plunger is then depressed again to expose the fiber and the organic analytes on the fiber are thermally desorbed and analyzed. The fiber remains in the analytical instrument during the analysis. When the analysis has been completed, the plunger is moved to the withdrawn position and the syringe is removed from the injection port. Various injection ports are suitable such as the "split-splitless" type or the "on-column" type.

While various types of syringes will be suitable, a HAMILTON 7000 (a trade mark) series syringe has been found to be suitable. The syringe facilitates convenient operation of the solid phase microextraction process and protects the fiber from damage during the introduction into a sample bottle or into an injector of an analytical instrument or even during storage. The length of the fiber depends on the injector of the analytical instrument with which the fiber will be used. Preferably, the fiber is mounted in a housing to a movable part so that the fiber is movable longitudinally within the housing. Still more preferably, the movable part moves a sufficient distance so that at least part of said fiber can be extended outside of said housing and retracted into said housing successively. The movable part is preferably an elongated member which extends partially outside of the housing. The part of the elongated member that extends partially outside of the housing preferably has a handle thereon. The elongated member can be a plunger.

In addition to the improved convenience of the present device and method, the method differs significantly in the extraction part of the process compared to the prior art solid phase extraction process using cartridges. The extraction process in accordance with the present invention does not require prior sampling of aqueous material since in-vivo or in-vitro sampling can be conveniently performed. The microextractor can be directly inserted into the fluid stream. The simple geometry of the fiber eliminates clogging caused by particle matter present in the samples. Also, due to the small size of the fiber, not all of the organic compounds are extracted but rather the equilibrium described by the partition coefficient between the water and organic stationary phase for a given analyte is established. Therefore, the solid phase microextraction method of the present invention can be made selective by appropriate choice of a specifically designed organic phase. The partitioning between the aqueous phase and the organic coating can be described through the distribution constant, K:

$$K = \frac{C_s}{C_{aq}} \quad (1)$$

where $C_s$ is the concentration in the stationary phase and $C_{aq}$ is the concentration in the water. The partition ratio, $k'$, is therefore:

$$k' = \frac{C_s V_s}{C_{aq} V_{aq}} = \frac{n_s}{n_{aq}} = K \frac{V_s}{V_{aq}} \quad (2)$$

where $n_s$ and $n_{aq}$ are the number of moles in the stationary and aqueous phases, respectively, and $V_s$ and $V_{aq}$ are the volmaes of the respective phases. Rearranging Eqn. 2 yields:

$$ns = K \frac{V_s n_{aq}}{V_{aq}} \quad (3)$$

substituting $C_{aq} V_{aq}$ for $n_{aq}$ results in:

$$n_s = KV_s C_{aq} = AC_{aq} \quad (4)$$

where $A = KV_s$

A linear relationship between concentration of analytes in aqueous samples and detector response is expected based upon the relationship in equation (4). The slope of the linearity curve can be used to determine the partition coefficient for a given analyte if the volume of the stationary phase is known. Furthermore, the sensitivity of the fiber can be adjusted by changing the volume (thickness or area) of the stationary phase.

The linear dynamic range of the method typically extends several orders of magnitude for coatings similar to chromatographic stationary phase materials. The limit of quantization depends on the partition coefficient and the thickness of the coating and can be as low as a few ppT (parts per trillion), which was obtained for chlorinated solvents. In this case the amount of the solvents extracted by a thick polyimide coating from a water sample is about 30 pg per component at a 1 µg/L concentration. This amount ensures not only ECD detection but will allow mass spectrometric identification and quantization.

Figure 4:
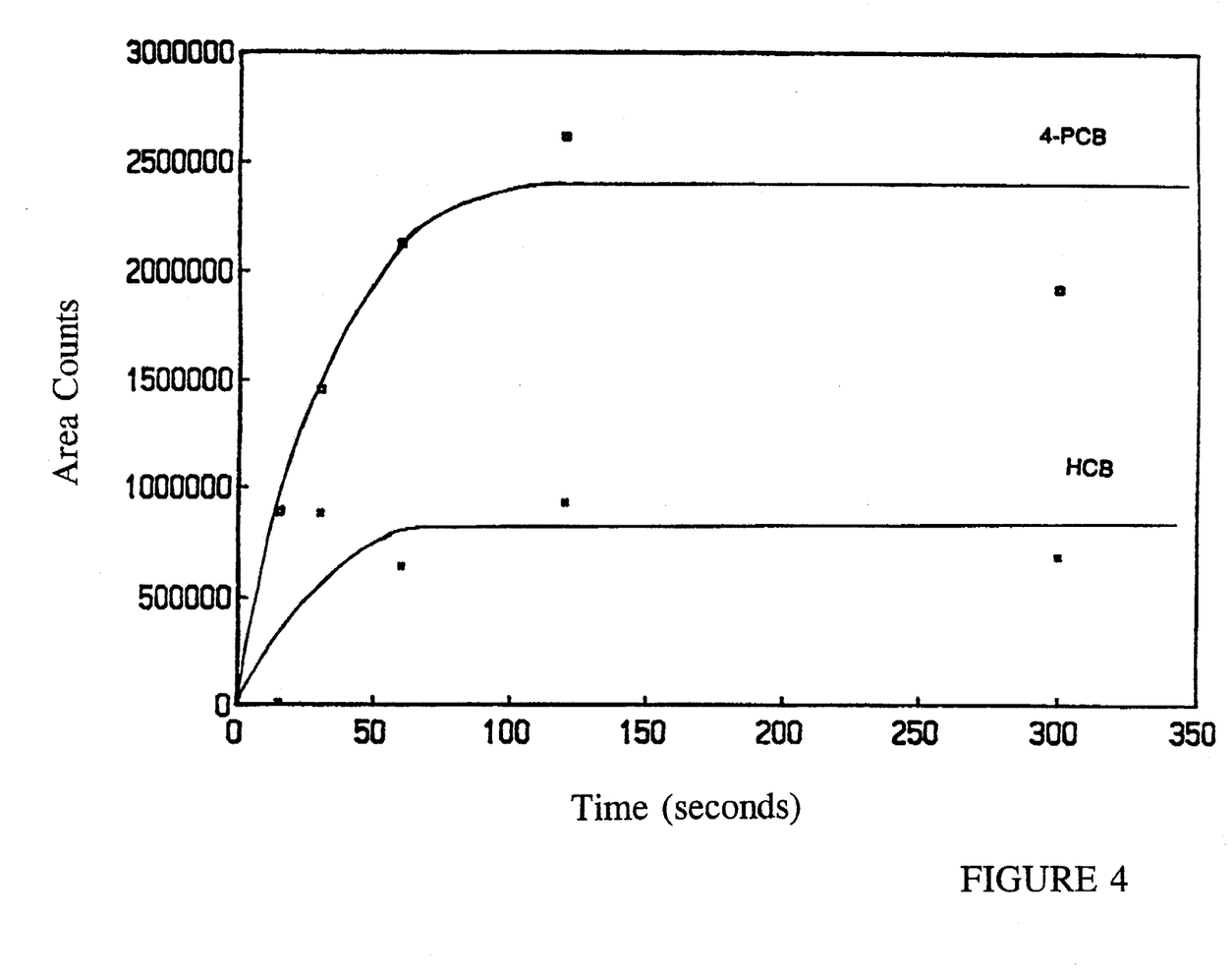
FIG. 4 is a graph of amount of analyte extracted versus time.

The dynamics of the extraction process is illustrated on FIG. 4 which shows an example of a typical relationship between the amount of analyte adsorbed onto the microextractor (peak area) versus the extraction time, which corresponds to the exposure time of the fiber to the water matrix sample. Initially, the amount of analyte adsorbed by the stationary phase increases with the increase in extraction time. This trend is continued until the point of steady state is achieved which causes the relationship to level off. This situation indicates the state of equilibrium between the concentration of the analyte in the stationary phase and in the water matrix sample and defines optimum extraction time. According to FIG. 3, optimum extraction time for uncoated fiber (about 0.1 µm film of silica gel) and PCBs as analytes is about one minute.

Figure 5:
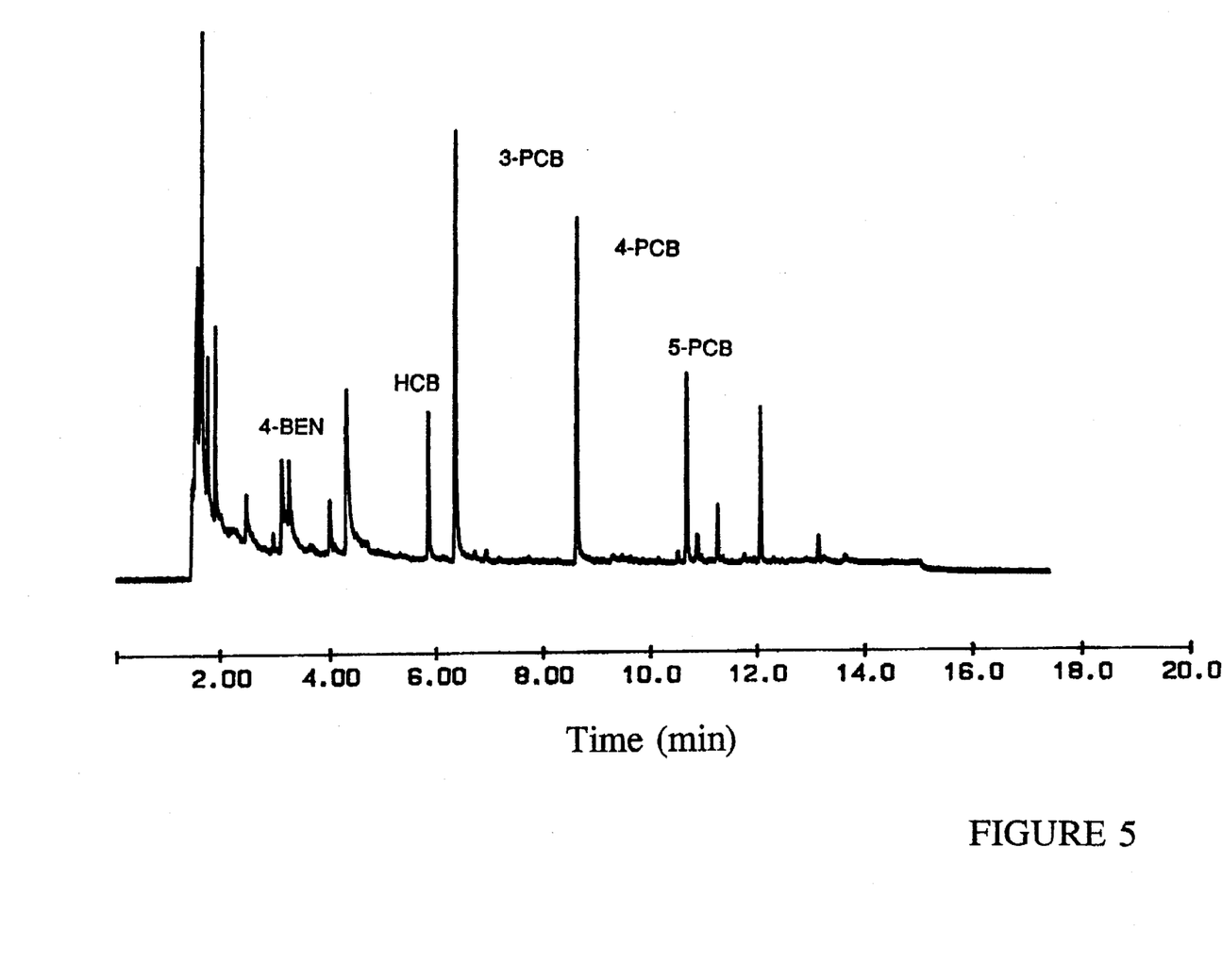
FIG. 5 is a graph showing the results of a typical gas chromatography analysis.

FIG. 5 illustrates the chromatogram corresponding to a PCB mixture in water extracted and analyzed by the solid phase microextraction method. Peak tailing is larger for the more volatile compounds than the heavier, later eluting components. This is an effect of thermal focussing that occurs when the analytes are volatilized at 300° C. and transferred to a 150° C. oven. The heavier compounds benefit from thermal focussing, but the oven is at too high a temperature to allow focussing of the more volatile compounds. The tailing can be alleviated by using a cryogenically cooled oven to improve focussing.

Figure 6:
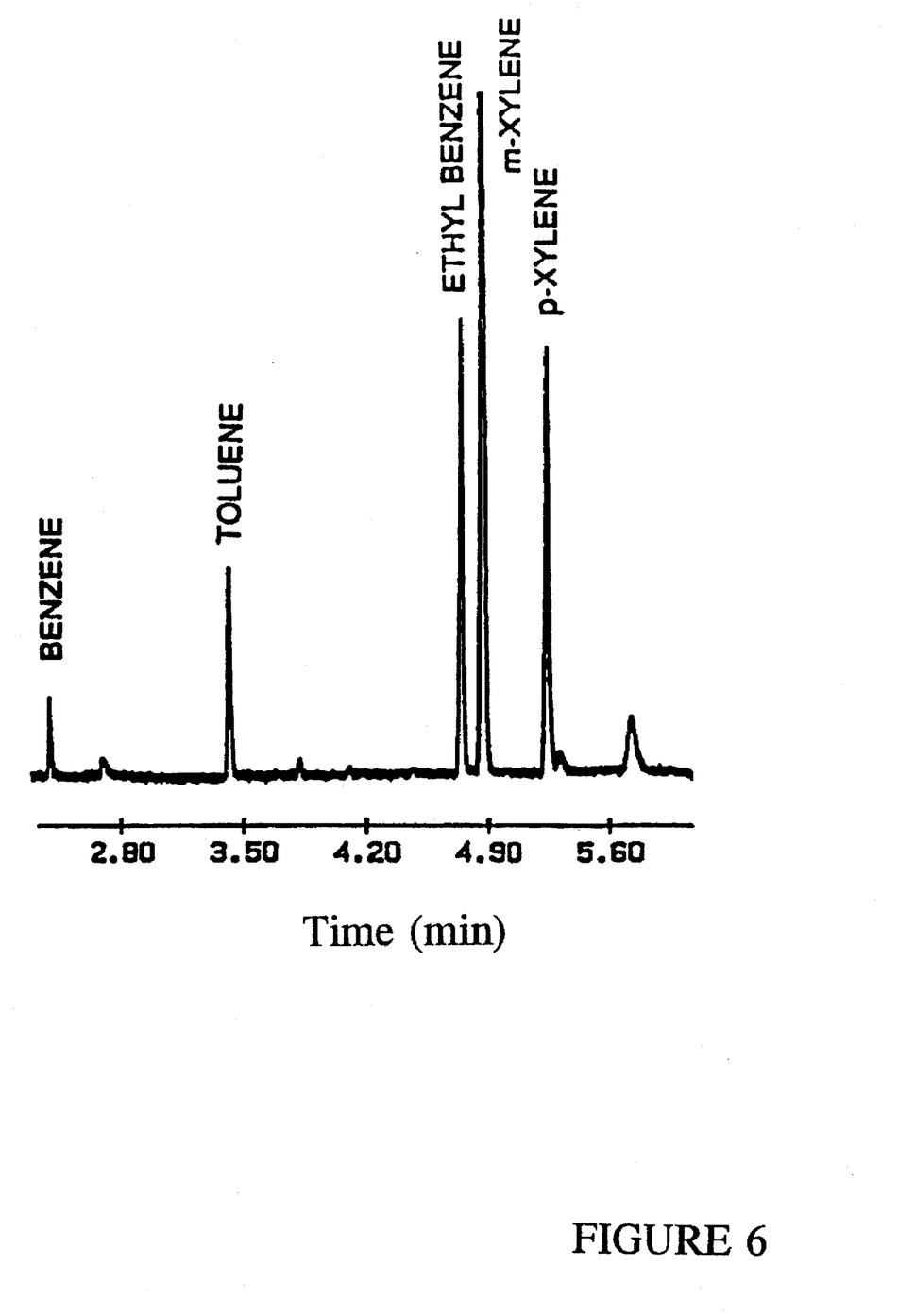
FIG. 6 is a graph showing another analysis from a gas chromatograph.

An uncoated fiber can also be used to adsorb benzene, toluene, ethyl benzene and xylenes (BTEX) from aqueous solutions. For this separation (FIG. 6), a flame ionization detector (FID) was used, illustrating that a sufficient quantity was adsorbed for FID detection. This expands the general applicability of the fiber as FID detectors are somewhat easier to operate and maintain than ECD detectors. The extraction efficiency in this case is sufficiently high to deplete significantly the analyte after 2 to 3 injections if a small volume of aqueous material (1 to 2 mL) is sampled. A larger sample volume (100 mL) is thus recommended if multiple injections are necessary.

Moderate levels of organic interferences and variation in ionic strength of aqueous solution do not significantly change the extraction equilibria. However, large amounts of organic solvent could be added intentionally to introduce partitioning selectivity, as is commonly done in liquid chromatography.

The fiber method has great potential for the analysis of highly sorptive compounds that can be difficult to sample without loss of analyte. Losses to storage bottles and transfer lines could potentially be eliminated by sampling in situ and analyzing the fiber in the field using portable gas chromatograph instrumentation. The device and method of the present invention can utilize a mechanical device such as an autosampler. The autosampler can be programmed to operate the plunger at the appropriate time to contact the carrier and to insert the syringe and the fiber into the injection port of the analytical instrument. The autosampler has an advantage over manual extraction and analysis in that the contact time and the length of the fiber in the carrier as well as in the instrument can be maintained constant. A VARIAN 3500 gas chromatograph and a VARIAN 8100 autosampler has been found to be suitable.

Possible applications of this technique include sampling of both surface and groundwater samples, either in situ or in the laboratory. It could potentially be used in on-line process applications or clinical analysis. Both of these applications benefit from the simplified sample preparation. The coating can be designed for either a broad scan of the organic contaminants (non-selective fiber coating) or selective sampling. This method, when combined with laser desorption, could reduce the sample extraction and analysis to a fraction of a minute. In this technique the optical fiber is used as a light guide. In a variation of the invention, the syringe could have a laser source affixed thereto with activation means and coupling optics to focus light onto the fiber which will transmit the light to a free end thereof to desorb the components thereon. Curie point heating and microwave desorption are alternative desorption methods. The fiber also shows promise as a method of studying the adsorption properties of polymers and for obtaining information about partitioning in liquid chromatographic systems.

Figure 7A:
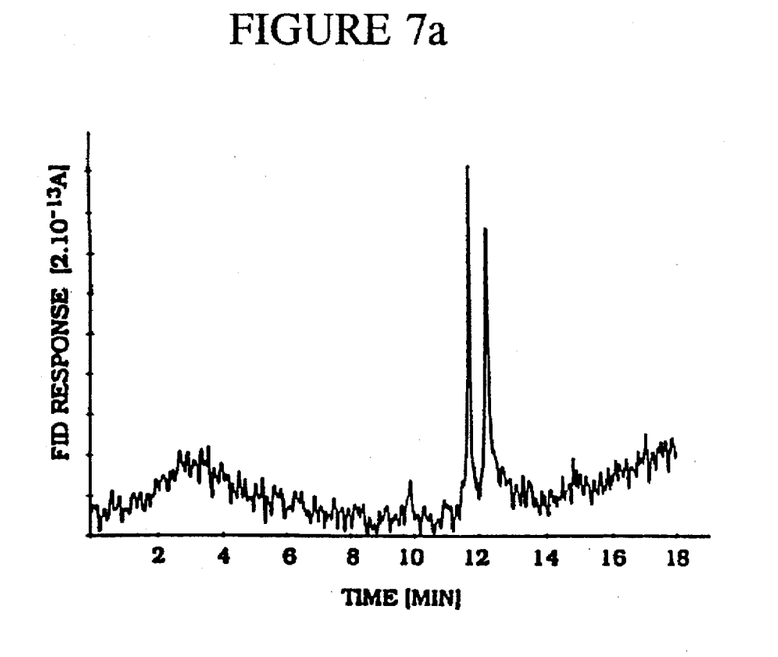
FIG. 7a shows a chromatogram produced when using the solid phase microextraction of the present invention.
Figure 7B:
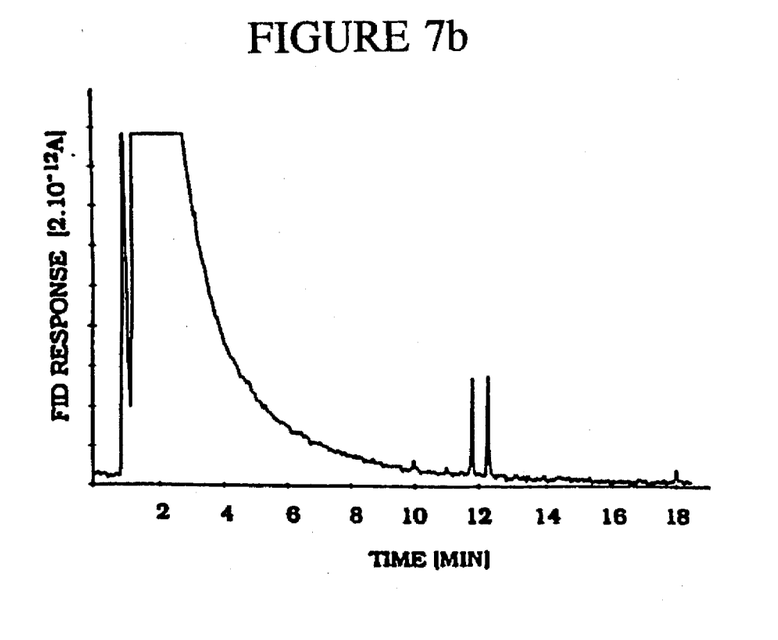

FIG. 7 illustrates the advantages of the method of the present invention compared to the prior art solvent procedure. The chromatogram from FIG. 7a corresponds to silica fiber techniques using C-18 coating and FIG. 7b to liquid-liquid extraction with chloroform. In both cases the same effluent from a sewage treatment plant was analyzed under the same chromatographic conditions. Results are similar, however the total extraction time was about an hour for the solvent method and two minutes for the fused silica fiber technique. The chromatogram for FIG. 7b shows the presence of the solvents used in the liquid-liquid extraction. The solid phase microextraction device facilitates easy sampling in the field. In addition, when organic solvents are used in the preparation step, the corresponding large peak together with possible impurities can mask volatile analytes (FIG. 7b).

Figure 8:
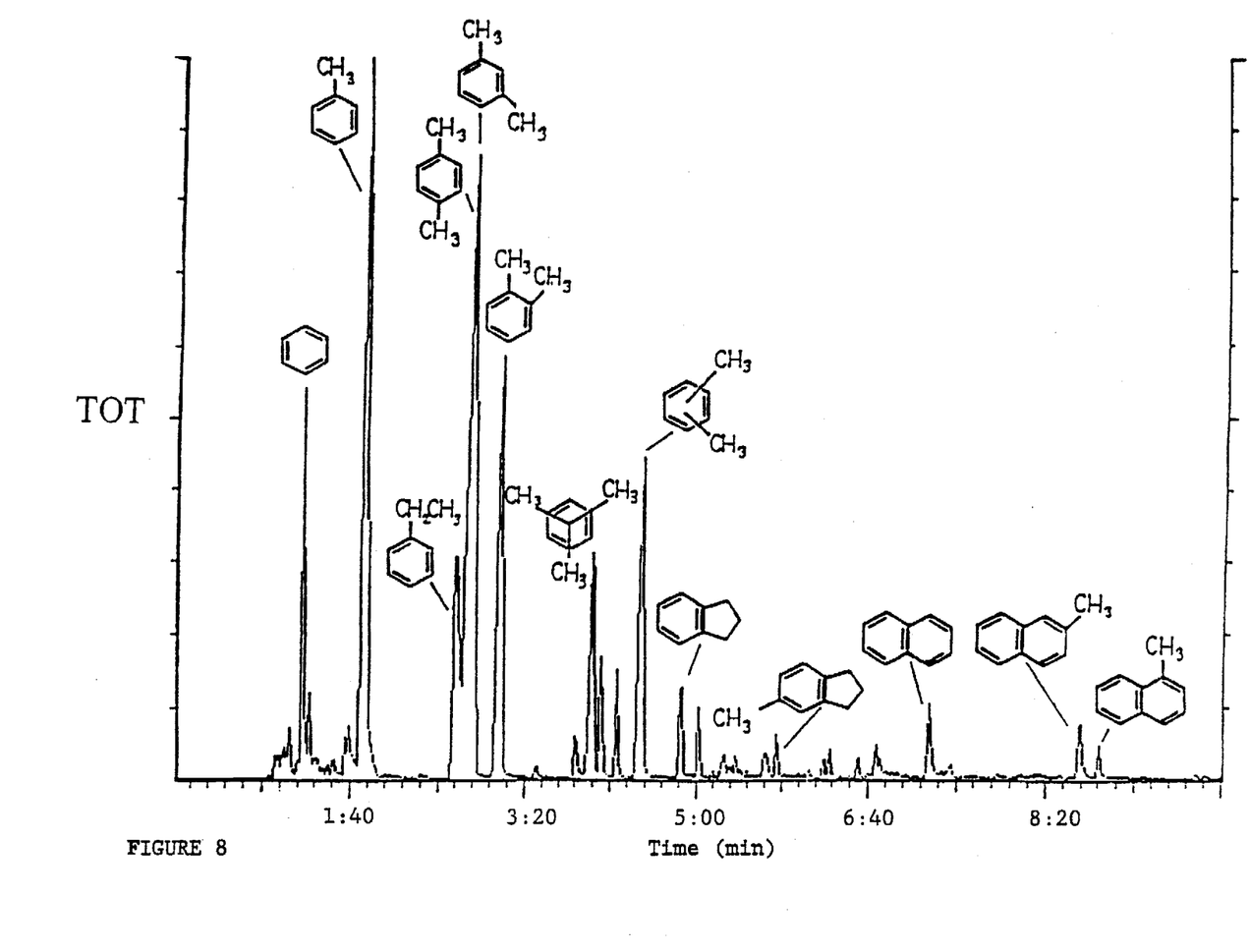
FIG. 8 is a chromatogram of the extraction of gasoline components from water with silicone coated fibers.
Figure 9:
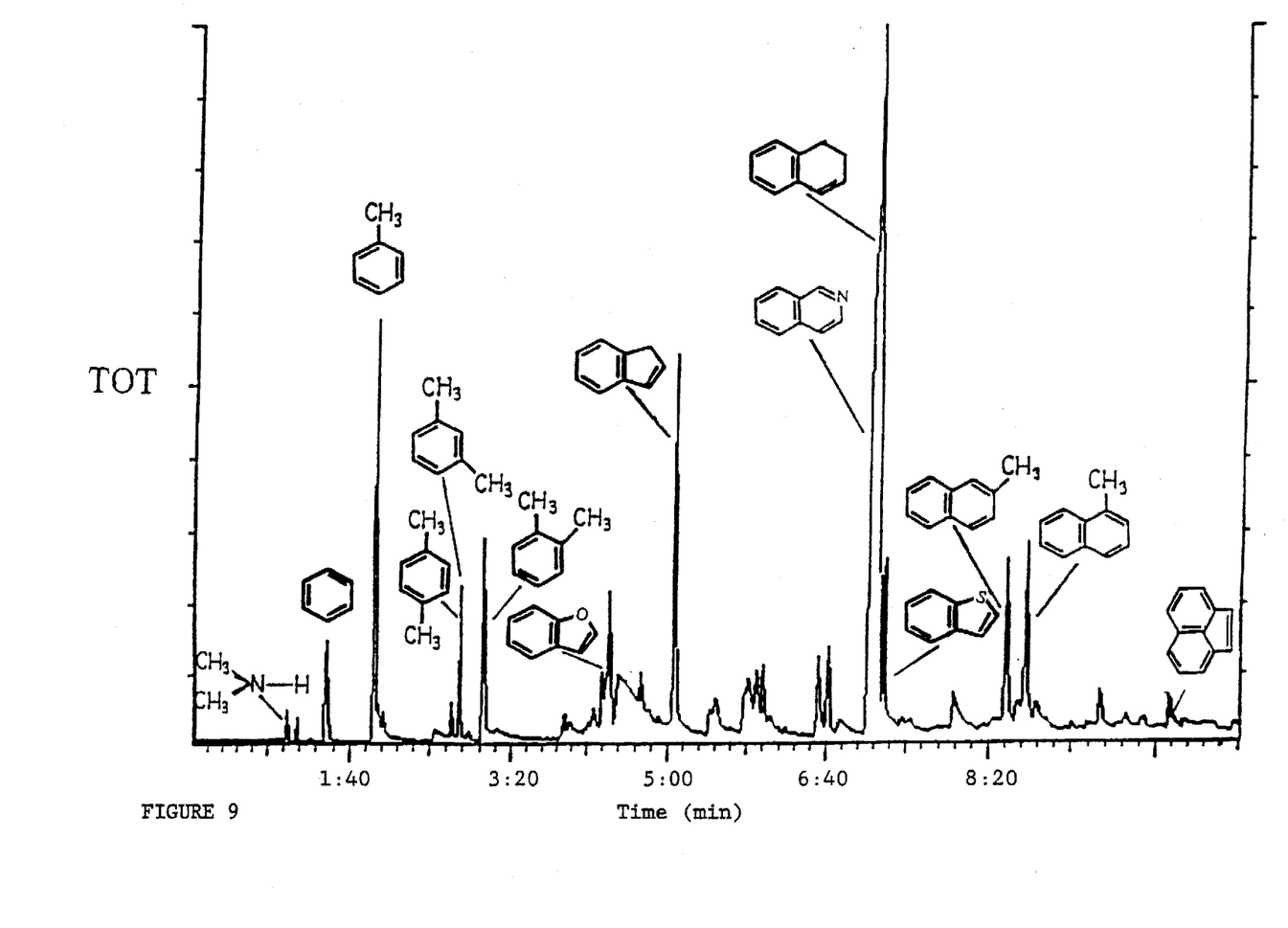
FIG. 9 is a chromatogram from the extraction of organics from coal gasification waste water using a silicone coated fiber.

In FIG. 8, there is shown a chromatograph for the extraction of gasoline components from water using a silicone coated fiber. In FIG. 9, there is shown a chromatograph for the extraction of organics from coal gasification waste water using a silicone coated fiber. Both analyses and identifications for FIGS. 8 and 9 have been done using a mass spectrometry detector.

The device and method of the present invention can also be used for extraction and analysis of gases and for supercritical fluids as well. The method is not limited to analysis of organic analytes but also for inorganic ions by using ion-exchange materials located on the fiber surface. In addition to thermal desorption by direct heating, laser desorption or conductive heating, for example, microwave desorption or Curie point magnetic hysteresis method could be used. Various fibers will be suitable depending on the use that is being made of the present invention. For example, fused silica, graphite fibers, fibers constructed with solid polymeric materials and even metal wires can be used as fibers and the fibers can be coated with various materials or uncoated. Some suggested coatings are CARBOWAX (a trade mark), octadecyltrichlorosilane, polymethylvinylchlorosilane, liquid crystalline polyacrylates, silicone, polyimide and grafted self-assembled monolayers. Fibers coated with these coatings are stored under nitrogen or helium to prevent absorption of the volatile organics present in air. The coatings can be organic or inorganic, for example, fused silica surface.

In addition to having coating located on an outer surface of a solid fiber, coating could be located on an inner surface of a hollow fiber. Coating could also be located on the packing material used with the fiber. In addition to direct extraction, the method of the present application could be performed with prior activation using organic solvents by using the optional inlet 26 on the syringe. The analytical instrument used with the method of the present invention can also be varied. For example, a gas chromatograph, a liquid chromatograph or a supercritical fluid chromatograph could be used. Other analytical methods such as flow injection analysis, mass spectrometry, atomic absorption or emission including inductively coupled plasma technique could be used.

In addition to analyzing for environmental contaminants, the method and device of the present invention can be used to monitor or measure the components in industrial process streams. The present invention can also be used to study properties of coatings, for example, absorption, deterioration rates and diffusion coefficients.

Numerous other variations, within the scope of the attached claims, will be readily apparent to those skilled in the art.

I claim:

1. A device for carrying out solid phase microextraction of components contained in a fluid carrier, said device being characterized by, in combination, a fiber and a housing surrounding said fiber, said fiber having means for selectively extracting at least one component in said fluid carrier, said fiber being mounted to a movable part in said housing so that said fiber is movable longitudinally within said housing, said movable part being able to successively expose a length of said fiber outside of said housing to said carrier and retract said fiber into said housing out of contact with said carrier.

2. A device as claimed in claim 1 wherein the movable part is an elongated member that is located within said housing, said elongated member extending partially outside of said housing, said fiber being mounted on said elongated member so that the fiber moves longitudinally with movement of said elongated member.

3. A device as claimed in claim 2 wherein the elongated member has a handle located on an end that protrudes from said housing.

4. A device as claimed in claim 3 wherein the elongated member is a plunger.

5. A device as claimed in claim 1 wherein the housing is a syringe having a barrel and plunger slidable within said barrel, said plunger having a handle extending from one end of said barrel, said fiber being mounted within said syringe so that said fiber will move longitudinally within said syringe as said plunger is moved within said barrel.

6. A device as claimed in claim 5 wherein a hollow needle is connected to said barrel at an end opposite to said handle, said needle containing said fiber, said fiber at least partially extending beyond a free end of said needle when said plunger is depressed within said barrel and said fiber being located within said needle when said plunger is withdrawn relative to said barrel.

7. A device as claimed in claim 6 wherein the fiber is partially contained in a metal sleeve within said syringe, said sleeve protecting the fiber from damage, said fiber extending from a plunger end of said barrel through said barrel and into said needle, said fiber having retention means thereon, said retention means being located at said plunger end of said barrel, said fiber being mounted to extend beyond said sleeve when said fiber is exposed outside of said housing.

8. A device as claimed in any one of claims 1, 5 or 6 wherein the fiber is hollow and there the are means for the carrier components to contact an interior surface of said fiber.

9. A device as claimed in claim 6 wherein the fiber is hollow and the needle contains openings so that said carrier and components can contact an interior of said fiber.

10. A device as claimed in any one of claims 1, 5 or 9 wherein the means by which the fiber selectively extracts at least one component in said fluid carrier is a coating on a surface of the fiber which coating is contacted by said carrier and components.

11. A device as claimed in claim 9 wherein the interior of the fiber is packed with a sorbent material.

12. A device as claimed in any one of claims 1, 5 or 6 wherein the fiber is hollow, an interior of the fiber being packed with sorbent material and the sorbent material being coated.

13. A device as claimed in any one of claims 1, 5 or 6 wherein said fiber is solid.

14. A device as claimed in any one of claims 1, 5 or 6 wherein said fiber is solid and the means by which the fiber selectively extracts at least one component in said fluid carrier is a coating on a surface of the fiber which coating is contacted by said carrier and components.

15. A device as claimed in any one of claim 5, 6 or 7 wherein the syringe contains a liquid inlet and a liquid outlet for said carrier to receive one of the group selected from an activation solvent and the carrier.

16. A device as claimed in any one of claims 1, 6 or 9 wherein the means by which the fiber selectively extracts at least one component in said fluid carrier is a coating on the fiber, wherein the coating is selected from the group of carbowax, silicone, polyimide, octadecyltrichlorosilane, polymethylvinylchlorosilane, liquid crystalline polyacrylates, grafted self-assembled monolayers and inorganic coatings.

17. A device as claimed in any one of claims 1, 6 or 9 wherein the fiber is selected from the group of fused silica fibers, graphite fibers, fibers made from solid polymeric materials and fibers made from metal wire.

18. A device as claimed in any one of claims 5, 6 or 7 wherein the syringe is connected to an autosampler, said autosampler being programmable to manipulate the plunger and to carry out extraction and analysis.

19. A device as claimed in any one of claims 5, 6 or 7 wherein the syringe has a laser source affixed to it, with activation means for said laser, light from said laser desorbing the fiber into an analytical instrument.

20. A method of carrying out solid phase microextraction and analysis with components contained in a carrier using a fiber contained in a housing, said housing having access means so that said carrier can be brought into contact with said fiber, said method comprising the steps of choosing either the fiber or a coating for the fiber based on selectivity of the fiber or the coating for at least one component contained in said carrier, contacting said fiber with said carrier for a sufficient time to allow chemical extraction to occur of said at least one component, ending said contact and placing the fiber in a suitable analytical instrument in such a manner that desorption occurs with respect to the at least one component extracted from said carrier by said fiber.

21. A method as claimed in claim 20 wherein the fiber is mounted to a movable part in said housing so that said fiber is movable longitudinally within said housing, said method including the steps of moving said movable part so that said fiber extends at least partially outside of said housing for a sufficient time to allow chemical extraction to occur, then moving said movable part in an opposite manner so that said fiber is retracted into said housing.

22. A method as claimed in claim 21 wherein the movable part is an elongated member extending partially outside of said housing, said fiber being mounted on said elongated member so that said fiber moves longitudinally with movement of said elongated member, said elongated member having a handle located on an end that protrudes from said housing, said method including the steps of moving said elongated member by moving said handle so that at least part of said fiber extends outside of said housing, moving said handle in an opposite direction so that said fiber is retracted into said housing.

23. A method of carrying out solid phase microextraction and analysis as claimed in claim 20 wherein the housing is a syringe, said syringe having a barrel and a plunger slidable within said barrel, said plunger having a handle extending from one end of said barrel, with a hollow needle extending from the other end of said barrel, said fiber being mounted within said syringe so that the fiber is located within the needle when the plunger is in a withdrawn position, said fiber extending beyond a free end of said needle when the plunger is in a depressed position, said method being characterized by depressing said plunger to expose said fiber, placing said syringe in contact with said carrier and said components of said carrier for a sufficient time to allow extraction to occur between said fiber and said components, moving said plunger to a withdrawn position to cause the fiber to return to an interior of said needle, subsequently placing the needle into an injection port of an analytical instrument, depressing said plunger to expose said fiber so that desorption will occur, subsequently moving said plunger to the withdrawn position and removing said needle from said injection port.

24. A method of carrying out solid phase microextraction and analysis as claimed in claim 23 wherein samples are analyzed and the samples are contained in containers having a septum for receiving the needle of the syringe, said method utilizing an analytical instrument having an injection port containing a septum for receiving said needle, said method being characterized by the steps of commencing with the plunger in a withdrawn position and the fiber located within said needle, placing said needle through the septum of a container containing a sample to be analyzed, depressing said plunger to cause said fiber to extend beyond said needle into contact with said sample, continuing said contact for a sufficient time to allow microextraction to occur, moving the plunger to the withdrawn position, removing the syringe from said container, inserting the needle of said syringe through the septum of said injection port of said analytical instrument, depressing the plunger to expose said fiber to said instrument in such a manner that desorption will occur between at least one component on said fiber and said instrument, subsequently moving the plunger to the withdrawn position and withdrawing said needle from said instrument.

25. A method as claimed in any one of claims 20, 23 or 24 wherein the carrier being analyzed is selected from the group of water, liquid, gas and supercritical fluids.

26. A method as claimed in any one of claims 20, 23 or 24 wherein the extraction and analysis are carried out automatically through the use of an autosampler.

27. A method as claimed in any one of claims 23 or 24 wherein the device has a laser source on the syringe, with activating means and coupling optics to focus laser light onto the fiber, said method including the step of activating said laser, said fiber transmitting the light from said laser to a free end of the fiber where the components are located thereby desorbing the components.

28. A method of carrying out solid phase microextraction and analysis, with components contained in a carrier, using a fiber, said method comprising the steps of choosing either the fiber or a coating for the fiber based on selectivity of the fiber or the coating for at least on component contained in said carrier, placing said fiber in contact with said carrier containing said components for a sufficient period of time for chemical extraction to occur of said at least one component, subsequently removing said fiber from said carrier and placing the fiber into a suitable analytical instrument and carrying out thermal desorption with respect to the at least one component extracted from said carrier by said fiber.

29. A method as claimed in claim 28 wherein the carrier is stirred while the fiber is placed into it.

30. A method as claimed in claim 28 wherein the fiber is placed in contact with said carrier for approximately two minutes.

31. A method as claimed in any one of claims 20 or 28 including the steps of choosing the fiber from the group consisting of fused silica fibers, graphite fibers, fibers made from soild polymeric materials and fibers made from metal wire.

32. A method as claimed in any one of claims 20 or 28 wherein the method includes the steps of choosing a coating for the fiber selected from the group consisting of CARBOWAX, silicone, polyimide, octasecyltrichlorosilane, polymethylyinylchorosilane, liquid crystalline polyacrylates, grated self-assembled monolayers and inorganic coatings.

* * * * *